United States Patent [19]

Loving

[11] 4,314,568
[45] Feb. 9, 1982

[54] VASCULAR STABILIZER
[75] Inventor: James A. Loving, Dallas, Tex.
[73] Assignee: Baxter Travenol Laboratories, Inc., Deerfield, Ill.
[21] Appl. No.: 111,355
[22] Filed: Jan. 11, 1980
[51] Int. Cl.³ .......................... A61B 17/12; A61M 5/00
[52] U.S. Cl. ................................. 128/327; 128/214 R; 128/215
[58] Field of Search ...................... 128/214, 215, 214.4, 128/214.2, 325, 327, 346

[56] References Cited

U.S. PATENT DOCUMENTS

| | | | |
|---|---|---|---|
| Re. 19,924 | 4/1936 | Cohen | 128/327 |
| 1,824,516 | 9/1931 | Tyvand | 128/133 |
| 2,185,571 | 1/1940 | Robinson | 128/327 |
| 2,234,961 | 3/1941 | Canada | 128/327 |
| 2,402,306 | 6/1946 | Turkel | 128/215 |
| 2,409,432 | 10/1946 | Hubbard | 128/216 |
| 3,046,984 | 7/1962 | Eby | 128/216 |
| 3,059,645 | 10/1962 | Hasbrouck et al. | 128/346 |
| 3,167,072 | 1/1965 | Stone et al. | 128/214 |
| 3,722,508 | 3/1973 | Roberts | 128/133 |
| 3,812,851 | 5/1974 | Rodriguez | 128/133 |
| 3,834,380 | 9/1974 | Boyd | 128/133 |
| 3,900,026 | 8/1975 | Wagner | 128/133 |
| 3,901,226 | 8/1975 | Scardenzan | 128/133 |
| 3,973,565 | 8/1976 | Steer | 128/214.4 |
| 4,006,744 | 2/1977 | Steer | 128/214 |
| 4,196,735 | 4/1980 | Ayer | 128/214 R X |
| 4,223,673 | 9/1980 | Harris | 128/215 |

FOREIGN PATENT DOCUMENTS

1003251 3/1952 France ................................ 128/133

Primary Examiner—Stephen C. Pellegrino
Attorney, Agent, or Firm—Richards, Harris & Medlock

[57] ABSTRACT

A disposable device for stabilizing a vessel during venipuncture is provided. The device includes two half body portions, each half body portion having a vascular stabilizing rib thereon. A living hinge portion connects the two half body portions and permits pivotal motion whereby the stabilizing ribs may be brought closer together while maintaining a parallel relationship therebetween. A step locking mechanism also is connected between the two half body portions which permits pivotal motion about the hinge portion in one direction only. The device is placed on the body of the patient so that the vessel subject to venipuncture lies between the two stabilizing ribs. The half body portions are then pivoted about the hinge portion so that the vessel is stabilized between the stabilizing ribs. In this manner, vessels of any dimension may be stabilized. The step locking mechanism prevents pivotal motion in the opposite direction destabilizing the vessel and also ensures that the device may only be used for a single venipuncture procedure, thereby preventing cross-contamination between patients. The device is removed immediately after venipuncture and disposed of.

12 Claims, 5 Drawing Figures

VASCULAR STABILIZER

TECHNICAL FIELD

This invention relates to a vascular stabilizer for use during venipuncture, and more particularly to a vascular stabilizer capable of stabilizing veins of diverse dimensions.

BACKGROUND ART

The use of venipuncture during treatment of a medical patient is almost universal. Venipuncture may be used for a variety of functions, such as introducing a catheter or syringe for nourishing a patient unable to be fed in the conventional manner, providing antibiotics or other drugs into the blood system of a patient or transfusing the blood of the patient. This technique requires the location and penetration of a blood vessel, usually a vein, within the body of a patient. After the vein is located, it must be maintained in a stabilized position during penetration of the vein by a hollow needle or other means for providing communication with the patients blood flowing within the vein. Should the vein not be stabilized, it is likely to roll or shift during the venipuncture procedure. This occurrence can cause the procedure to fail or even lead to more serious consequences to the patient such as hemorrhaging.

At present, a person performing a venipuncture procedure on a patient typically will put tension on the skin by stretching it with their fingers to prevent the vein from rolling during the venipuncture. This technique requires one hand be employed in stabilizing the vein and is not always successful due to the location of the vein, or particular problems associated with the patient.

Typical prior art devices that attempt to stabilize the vein during a venipuncture procedure are described and claimed in U.S. Pat. No. 1,824,516 issued to Tyvand on Sept. 22, 1931 and entitled "Vein Retainer" and U.S. Patent Application Ser. No. 939,433 filed Sept. 5, 1978. In addition, French Pat. No. 1,003,251 issued to Roos and published on Mar. 17, 1952 discloses a related device.

Such prior art devices, except for the Tyvand patent, do not permit the device to be adjusted for stabilizing the broad range of vein dimensions encountered during venipuncture procedures. The Tyvand patent discloses a device having retaining fingers, between which a vein may be centered, that are adjustable with respect to each other. This device is designed to be reused, and therefore needs to be sterilized for each application to prevent cross contamination between patients. In addition, the means for adjusting the retaining fingers necessitate rotating a knob secured to a threaded shaft which requires a substantial input of time.

A need has thus arisen for a vascular stabilizing device that is simple and cheap to manufacture so that it may be disposable to prevent cross-contamination between patients. Additionally, a need has arisen for a vascular stabilizing device that is capable of being rapidly adjusted to the dimensions of the vein undergoing the venipuncture.

DISCLOSURE OF THE INVENTION

In accordance with the present invention, a vascular stabilizer is provided for stabilizing a vein during a venipuncture procedure. The device includes two half body portions connected by a hinge member. Each half body portion has a stabilizing edge portion thereon. The stabilizing edge portions define an elongated slot between the half body portions. Means are provided to secure each of the half body portions in contact with the patient so that the vein to be stabilized lies within the elongated slot formed by the two half portions of the body and defined by the stabilizing edge portions. The two half body portions are then pivoted with respect to each other about the hinge member to adjust the size of the slot so that the vein is stabilized between the stabilizing edge portions. A locking mechanism is provided that will not permit the half body portions to pivot from the position stabilizing the vein.

BRIEF DESCRIPTION OF THE DRAWINGS

A more complete understanding of the invention and its advantages will be apparent from the following detailed description taken in conjunction with the accompanying drawings in which.

DETAILED DESCRIPTION

Figure 1:
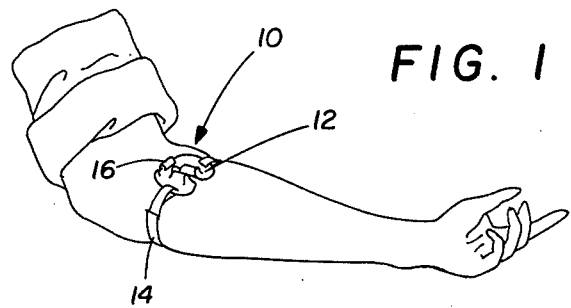
FIG. 1 is a perspective view of the vascular stabilization device secured about the arm of a patient.
Figure 2:
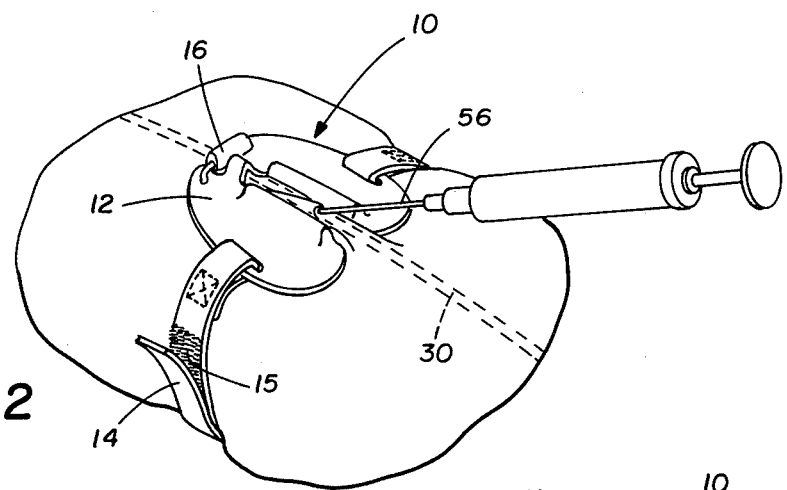
FIG. 2 is a perspective view of the vascular stabilization device secured about a portion of the arm of a patient and adjusted to stabilize a vein for penetration by an injection needle.

FIGS. 1 and 2 illustrate the preferred embodiment of the vascular stabilization device forming the present invention and generally identified by numeral 10. The vascular stabilization device 10 includes a flexible body 12, a hold down strap 14 and a step locking mechanism 16. All elements of the vascular stabilization device 10 are formed from disposable plastic materials that are sterilized and transported to the hospital or doctor within enclosures that maintain sterility until time for use.

Figure 3:
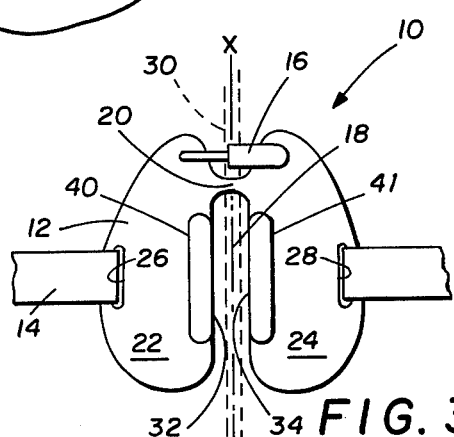
FIG. 3 is a top view of the vascular stabilization device of the present invention.

As illustrated in FIG. 3, the flexible body 12 has a slot 18 formed therein which extends almost the entire way through flexible body 12, leaving a living hinge portion 20 maintaining the integrity of the flexible body 12. Slot 18 separates the body 12 into two half body portions 22 and 24. Living hinge portion 20 is designed to permit pivotal motion between half body portions 22 and 24 about axis X—X as shown in FIG. 3, but no other. Half body portions 22 and 24 have slits 26 and 28 respectively at the outer edge thereof opposite slot 18. Slits 26 and 28 form attachment points for the two ends of hold down strap 14. Strap 14 is formed in two sections to permit the strap to be placed around the arm, leg or other body member of the patient. The two sections are then joined by means such as Velcro 15 to form an inexpensive but strong connection. The step locking mechanism 16 lies near hinge portion 20 and is connected at one end to half body portion 22 and at the other end to half body portion 24. Flexible body 12 is preferably molded with slot 18 therein.

Figure 4:
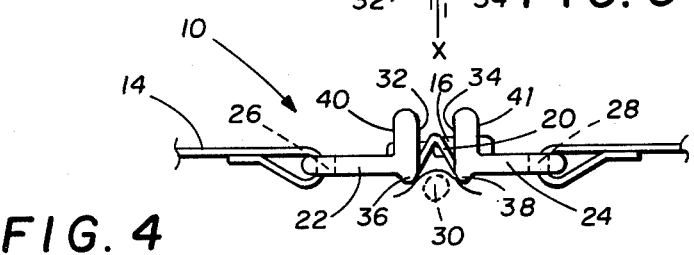
FIG. 4 is an end view of the vascular stabilization device of the present invention.

The slot 18 is formed such that the dimension along the length of the slot 18 is relatively much larger than the dimension across the width of slot 18. The device 10 is oriented on the patient so that the vein 30 to be pierced is centered in slot 18 between the stabilizing edges 32 and 34 of body portions 22 and 24. Edges 32 and 34 form the parallel longitudinal side walls of slot 18 and extend along the slot 18 in the longitudinal dimension. The vein 30 is stabilized by pivoting half body portions 22 and 24 about the living hinge portion 20 so that stabilizing ribs 36 and 38, projecting downwardly from the edges 32 and 34 as best shown in FIG. 4, confine vein 30 to a stabilized position. The living hinge portion 20 is sufficiently rigid in a direction perpendicular to the pivotal axis X—X so that stabilizing edges 32 and 34 and stabilizing ribs 36 and 38 are maintained in a parallel relation. It is clear that veins of varied dimensions may be stabilized by device 10 by pivoting half body portions 22 and 24 the degree necessary to accomodate the vein as the width of slot 18 is designed to accomodate the largest vein encountered in venipuncture. The rotation of half body portions 22 and 24 is facilitated by means of finger grips 40 and 41 projecting from the top portion of edges 32 and 34 of the device 10. The half body portions 22 and 24 are then held in their rotated positions by means of step locking mechanism 16.

Figure 5:
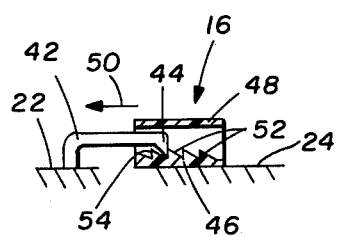
FIG. 5 is a cross-sectional view of the step locking mechanism.

As best illustrated in FIG. 5, step locking mechanism 16 comprises a pin 42 with a hooked portion 44 at its head interacting with a toothed rack 46 within enclosed structure 48. Pin 42 is attached at its opposite end to half body portion 22. Toothed rack 46 and enclosed structure 48 are attached to half body portion 24. It is clear from the structure of step locking mechanism 16 that the half body portions 22 and 24 may be pivoted relative to one another about living hinge portion 20 in one direction with little effort. In this direction pin 42 moves in the direction indicated by arrow 50. The hooked portion 44 begins to move upward on slopes 52 of the toothed rack 46 until the top edge is reached, at which time the hooked portion 44 moves down vertical side 54 of the toothed rack 46. The resiliency of pin 42 permits this movement to be relative effortless, however, it is clear that motion in a direction opposite to arrow 50 is prevented by the interaction of the head of pin 42 and the vertical side 54 of toothed rack 46.

In operation, the vascular stabilization device 10 is employed by securing the device 10 about a body member of the patient by hold down strap 14. The Velcro surface 15 allows the hold down strap 14 to be adjusted in length for the individual patient. It is clear any other securing means, such as tape or adhesive may be substituted for strap 14 if so desired. The device 10 is positioned so that the vein 30 to be penetrated lies along slot 18 between edges 32 and 34. The force exerted by device 10 against the patient in securing the device in this position acts to draw the vein 30 nearer the skin, thereby simplifying the venipuncture. It is clear that the vein 30 may be of any size as the width of slot 18 is designed to accomodate the largest vein encountered during venipuncture. Half body portions 22 and 24 are then pivoted relative to each other around living hinge portion 20 so that stabilizing ribs 36 and 38 move into a position adjacent the walls of vein 30 whereby vein 30 is immobilized as best illustrated in FIG. 4. During this rotation, pin 42 moves in the direction of arrow 50 relative to toothed rack 44, and prevents any possibility of the stabilizing ribs 36 and 38 moving apart from each other to destabilize the vein 30. Upon stabilization, vein 30 may be penetrated by a suitable needle 56 or other device as illustrated in FIG. 2. After insertion of the needle 56, the vascular stabilization device 10 is released from the body member by unhooking hold down strap 14 and the device 10 is disposed of.

The vascular stabilization device 10 of the present invention thereby permits rapid and efficient stabilization of a vein to be penetrated in a venipuncture procedure without regard to the size of the vein. In addition, the device 10 is manufactured of materials and has a structure permitting the device 10 to be disposed of after a single use, thereby preventing cross contamination of patients possible with a vascular stabilization device that is designed for reuse. The vascular stabilization device 10 is designed to be used only during the venipuncture procedure and is to be removed immediately thereafter. The device 10 is therefore designed so that it may be released before the needle 56 or other indwelling probe is removed. The step locking mechanism 16 permits the vascular stabilization device 10 to be adjusted in only one direction, thereby preventing destabilization of the vein or reuse of the device 10 by mistake.

While only one embodiment of the present invention has been described in detail herein and shown in the accompanying drawings, it will be evident that various further modifications are possible without departing from the scope of the invention.

I claim:

1. An adjustable vascular stabilization device for stabilizing a blood vessel during venipuncture comprising:
   a first body portion, said first portion having a first stabilizing edge portion thereon;
   a second body portion, said second body portion having a second stabilizing edge portion thereon;
   hinge means connecting said first and second body portions;
   means securing said first body portion and said second body portion in contact with a patient with the portion of the vessel subject to venipuncture lying between said first stabilizing edge portion and said second stabilizing edge portion;
   said first and second body portions being pivotal from an initial position about said hinge means to a stabilizing position to stabilize said vessel during venipuncture, said vessel being stabilized between said first and second stabilizing edge portions; and
   locking means preventing said first and second body portions from pivoting about said hinge means from the position stabilizing said vessel, said locking means permitting said first and second body portions to pivot freely from the initial position to the stabilizing position.

2. The adjustable vascular stabilization device of claim 1 wherein said first and second body portions are formed of flexible material and said hinge means comprises a living hinge formed integral with said first and second body portions.

3. An adjustable vascular stabilization device for stabilizing a blood vessel during venipuncture comprising:
   a first body portion, said first body portion having a first stabilizing edge portion thereon;
   a second body portion, said second body portion having a second stabilizing edge portion thereon;
   hinge means connecting said first and second body portions;
   means securing said first body portion and said second body portion in contact with a patient with the portion of the vessel subject to venipuncture lying between said first stabilizing edge portion and said second stabilizing edge portion;

said first and second body portions being pivotal about said hinge means to stabilize said vessel during venipuncture, said vessel being stabilized between said first and second stabilizing edge portions; and locking means preventing said first and second body portions from pivoting about said hinge means from the position stabilizing said vessel, said locking means including a flexible pin attached at a first end to said first body portion, the second end, opposite said first end, having hook means thereon and an enclosed structure attached to said second body portion and receiving said pin therein, said structure containing a toothed rack therein for engaging said hook means on said pin and preventing pivotal motion about said hinge means in one direction while permitting pivotal motion in the opposite direction.

4. The adjustable vascular stabilization device of claim 1 wherein said first and second stabilizing edge portions comprise:

first and second stabilizing rib portions extending from the side of said first and second body portions in contact with the patient, said vessel being stabilized between said first and second stabilizing rib portions; and first and second finger grips extending from the side of said first and second body portions opposite said side in contact with the patient for pivoting said first and second body portions about said hinge means during venipuncture.

5. An adjustable vascular stabilization device for stabilizing a blood vessel during venipuncture comprising:

a first body portion, said first body portion having a first stabilizing edge portion thereon;

a second body portion, said second body portion having a second stabilizing edge portion thereon;

hinge means hingeably connecting said first and second body portions;

means securing said first and second body portions in contact with a patient with the portion of the vessel subject to venipuncture lying between the first and second stabilizing edge portions;

said first and second body portions being pivotal from an initial position about said hinge means to a stabilizing position to adjust for vessels of varied dimensions and to stabilize said vessel during venipuncture, said vessel being stabilized between said first and second stabilizing edge portions; and locking means preventing said first and second body portions from pivoting about said hinge means from said stabilizing position stabilizing said vessel, said locking means further preventing reuse of said device, said locking means permitting the first and second body portions to pivot freely from the initial position to the stabilizing position.

6. The adjustable vascular stabilization device of claim 5 wherein said first and second body portions are formed of flexible material and said hinge means comprises a living hinge formed integral with said first and second body portions.

7. An adjustable vascular stabilization device for stabilizing a blood vessel during venipuncture comprising:

a first body portion, said first body portion having a first stabilizing edge portion thereon;

a second body portion, said second body portion having a second stabilizing edge portion thereon;

hinge means hingeably connecting said first and second body portions;

means securing said first and second body portions in contact with a patient with a portion of the vessel subject to venipuncture lying between said first and second stabilizing edge portions;

said first and second body portions being pivotal about said hinge means to adjust for vessels of varied dimensions and to stabilize said vessel during venipuncture, said vessel being stabilized between said first and second stabilizing edge portions; and locking means preventing said first and second body portions from pivoting about said hinge means from said position stabilizing said vessel, said locking means further preventing reuse of said device, said locking means including a flexible pin attached at a first end to said first body portion, the second end, opposite said first end, having hook means thereon and an enclosed structure attached to said second body portion and receiving said pin therein, said structure containing a toothed rack therein for engaging said hook means on said pin and preventing pivotal motion about said hinge means in one direction while permitting pivotal motion in the opposite direction.

8. The adjustable vascular stabilization device of claim 5 wherein said first and second stabilizing edge portions comprise:

first and second stabilizing rib portions extending from the side of said first and second body portions in contact with the patient, said vessel being stabilized between said first and second stabilizing rib portions; and first and second finger grips extending from the side of said first and second body portions opposite said side in contact with the patient for pivoting said first and second body portions about said hinge means during venipuncture.

9. An adjustable vascular stabilization device for stabilizing a blood vessel during venipuncture comprising:

a first body portion, said first body portion having a first stabilizing edge portion thereon;

a second body portion, said second body portion having a second stabilizing edge portion thereon;

hinge means hingeably connecting said first and second body portions and maintaining said first and second stabilizing edge portions in a parallel relationship;

means securing said first and second body portions in contact with a patient with the portion of the vessel subject to venipuncture lying between said first and second stabilizing edge portions;

said first and second body portions being pivotal from an initial position about said hinge means to a stabilizing position to adjust for vessel of varied dimensions and to stabilize the vessel during venipuncture, said vessel being stabilized between said first and second stabilizing edge portions; and locking means for preventing said first and second body portions from pivoting about said hinge means from said stabilizing position stabilizing said vessel, said locking means further preventing reuse of said device, said locking means permitting said first and second body portions to pivot from the initial position to the stabilizing position with little effort.

10. The adjustable vascular stabilization device of claim 9 wherein said first and second body portions are formed of flexible material and said hinge means comprises a living hinge formed integral with said first and second body portions.

11. An adjustable vascular stabilization device for stabilizing a blood vessel during venipuncture comprising:

a first body portion, said first body portion having a first stabilizing edge portion thereon;

a second body portion, said second body portion having a second stabilizing edge portion thereon;

hinge means hingeably connecting said first and second body portions and maintaining said first and second stabilizing edge portions in a parallel relationship;

means securing said first and second body portions in contact with a patient with the portion of the vessel subject to venipuncture lying between said first and second stabilizing edge portions;

said first and second body portions being pivotal about said hinge means to adjust for vessels of varied dimensions and to stabilize the vessel during venipuncture, said vessel being stabilized between said first and second stabilizing edge portions; and locking means preventing said first and second body portions from pivoting about said hinge means from said position stabilizing said vessel, said locking means further preventing reuse of said device, said locking means including a flexible pin attached at a first end to said first body portion, the second end, opposite said first end, having hook means thereon; and an enclosed structure attached to said second body portion and receiving said pin therein, said structure containing a toothed rack therein for engaging said hook means on said pin and preventing pivotal motion about said hinge means in one direction while permitting pivotal motion in the opposite direction.

12. The adjustable vascular stabilization device of claim 9 wherein said first and second stabilizing edge portions comprise:

first and second stabilizing rib portions extending from the side of said first and second body portions in contact with the patient, said vessel being stabilized between said first and second stabilizing rib portions; and first and second finger grips extending from the side of said first and second body portions opposite said side in contact with the patient for pivoting said first and second body portions about said hinge means during venipuncture.

* * * * *